United States Patent

(12) United States Patent
Furukawa et al.

(10) Patent No.: US 10,940,105 B2
(45) Date of Patent: *Mar. 9, 2021

(54) RESIN-LINEAR ORGANOPOLYSILOXANE BLOCK COPOLYMER, USE OF SAME, AND METHOD FOR PRODUCING SAME

(71) Applicants: DOW TORAY CO., LTD., Tokyo (JP); DOW SILICONES CORPORATION, Midland, MI (US)

(72) Inventors: Haruhiko Furukawa, Ichihara (JP); John Bernard Horstman, Midland, MI (US); Tomohiro Iimura, Ichihara (JP); Tadashi Okawa, Ichihara (JP); Steven Swier, Midland, MI (US)

(73) Assignees: Dow Silicones Corporation, Midland, MI (US); Dow Toray Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/339,290

(22) PCT Filed: Oct. 3, 2017

(86) PCT No.: PCT/JP2017/036021
§ 371 (c)(1),
(2) Date: Apr. 3, 2019

(87) PCT Pub. No.: WO2018/066572
PCT Pub. Date: Apr. 1, 2018

(65) Prior Publication Data
US 2019/0231674 A1   Aug. 1, 2019
US 2020/0253855 A9   Aug. 13, 2020

Related U.S. Application Data

(60) Provisional application No. 62/403,951, filed on Oct. 4, 2016, provisional application No. 62/403,955, filed on Oct. 4, 2016.

(51) Int. Cl.
| | | |
|---|---|---|
| *C08G 77/44* | (2006.01) |
| *A61K 8/891* | (2006.01) |
| *A61Q 19/00* | (2006.01) |
| *A61K 8/894* | (2006.01) |
| *C08L 83/10* | (2006.01) |
| *A61K 8/06* | (2006.01) |
| *A61K 8/34* | (2006.01) |
| *A61K 8/90* | (2006.01) |
| *A61Q 1/02* | (2006.01) |
| *A61Q 17/04* | (2006.01) |
| *C08G 77/42* | (2006.01) |
| *C08G 77/46* | (2006.01) |
| *C08G 77/16* | (2006.01) |

(52) U.S. Cl.
CPC .............. *A61K 8/891* (2013.01); *A61K 8/062* (2013.01); *A61K 8/064* (2013.01); *A61K 8/34* (2013.01); *A61K 8/894* (2013.01); *A61K 8/90* (2013.01); *A61Q 1/02* (2013.01); *A61Q 19/00* (2013.01); *C08L 83/10* (2013.01); *A61K 2800/10* (2013.01); *A61Q 17/04* (2013.01); *C08G 77/16* (2013.01); *C08G 77/42* (2013.01); *C08G 77/46* (2013.01)

(58) Field of Classification Search
CPC .......... C08G 77/16; C08G 77/44; C08L 83/10
See application file for complete search history.

(56) References Cited

U.S. PATENT DOCUMENTS

| | | | |
|---|---|---|---|
| 2,736,721 | A | 2/1956 | Dexter |
| 7,261,877 | B2 | 8/2007 | Luo et al. |
| 9,765,192 | B2* | 9/2017 | Horstman ............... C08L 83/10 |
| 2003/0091523 | A1 | 5/2003 | Dhamdhere et al. |
| 2007/0196309 | A1 | 8/2007 | Tarletsky et al. |
| 2010/0215595 | A1 | 8/2010 | Kennan et al. |
| 2012/0046486 | A1 | 2/2012 | Henning et al. |
| 2015/0340839 | A1 | 11/2015 | Zhang et al. |
| 2016/0208055 | A1* | 7/2016 | Horstman ............... C08G 77/20 |
| 2017/0152411 | A1 | 6/2017 | Mihara et al. |

FOREIGN PATENT DOCUMENTS

| | | | |
|---|---|---|---|
| JP | H02137737 | A | 5/1990 |
| JP | H08143426 | A | 6/1996 |
| JP | 2006504603 | A | 2/2006 |
| JP | 2010065221 | A | 3/2010 |
| JP | 2010540727 | A | 12/2010 |

(Continued)

OTHER PUBLICATIONS

English translation of International Search Report for International Application No. PCT/JP2017/036021 dated Dec. 5, 2017, 1 page.

(Continued)

*Primary Examiner* — Margaret G Moore
(74) *Attorney, Agent, or Firm* — Warner Norcross + Judd LLP

(57) ABSTRACT

Provided is a resin-linear organopolysiloxane block copolymer which has a high degree of freedom in formulation due to excellent compatibility with other materials, in addition to exhibiting excellent film forming properties and followability of a film, while the stickiness of a film is suppressed. The resin-linear organopolysiloxane block copolymer has: a resin structure (A1) block that has siloxane units represented by $R^1SiO_{3/2}$ (wherein $R^1$ represents a monovalent organic group, a hydroxyl group, or an alkoxy group having 1 to 6 carbon atoms) and $SiO_{4/2}$; and a linear structure (A2) block represented by $(R_2SiO_{2/2})_n$ (wherein n represents a number of 5 or more while R represents an alkyl group, a fluoroalkyl group, or an aryl group) in each molecule. The resin structure (A1) and the linear structure (A2) are linked to each other by an Si—O—Si bond, and an Si atom bonded to the resin structure (A1) constitutes an $RSiO_{3/2}$ unit.

13 Claims, No Drawings

(56) References Cited

FOREIGN PATENT DOCUMENTS

| JP | 2012184353 | A | | 9/2012 |
|---|---|---|---|---|
| WO | 0007550 | A1 | | 2/2000 |
| WO | 2004037941 | A2 | | 5/2004 |
| WO | 2004084847 | A1 | | 10/2004 |
| WO | 2005063890 | A2 | | 7/2005 |
| WO | 2012040367 | A1 | | 3/2012 |
| WO | 2012106391 | A1 | | 8/2012 |
| WO | 2013142138 | A1 | | 9/2013 |
| WO | 2014040367 | A1 | | 3/2014 |
| WO | 2014151464 | A1 | | 9/2014 |
| WO | 2014151587 | A2 | | 9/2014 |
| WO | 2014152522 | A1 | | 9/2014 |
| WO | 2015/042285 | | * | 3/2015 |
| WO | 2016031551 | A1 | | 3/2016 |

OTHER PUBLICATIONS

English translation of International Search Report for International Application No. PCT/JP2017/035985 dated Dec. 19, 2017, 1 page.
Machine assisted translation of JPH02137737A obtained from https://worldwide.espacenet.com on Mar. 29, 2019, 13 pages.
Machine assisted translation of JPH08143426A obtained from https://worldwide.espacenet.com on Apr. 2, 2019, 11 pages.
Machine assisted translation of JP2012184353A obtained from https://worldwide.espacenet.com on Mar. 29, 2019, 33 pages.

* cited by examiner

RESIN-LINEAR ORGANOPOLYSILOXANE BLOCK COPOLYMER, USE OF SAME, AND METHOD FOR PRODUCING SAME

CROSS-REFERENCE TO RELATED APPLICATIONS

This application is the National Stage of International Application No. PCT/JP2017/036021 filed on 3 Oct. 2017, which claims priority to and all advantages of U.S. Provisional Appl. Nos. 62/403,951 and 62/403,955 filed on 4 Oct. 2016, the contents of which is hereby incorporated by reference.

TECHNICAL FIELD

The present invention provides a novel resin-linear organopolysiloxane block copolymer, along with the use and production method thereof.

BACKGROUND ART

Unlike organopolysiloxane having a resin or linear structure alone, resin-linear organopolysiloxane block copolymers both having a resin structure consisting of branched siloxane units; and a linear (chain) structure consisting of disiloxane units in the same molecule are used in various applications due to their unique physical properties such as film forming properties derived from their resin structure, along with film followability and flexibility derived from their linear structure, in addition to excellent curing properties and film forming properties. Examples of such a resin-linear organopolysiloxane block copolymer include a condensation reaction product of an organopolysiloxane having a resin structure and an organopolysiloxane having a linear structure and the like.

For example, Patent Documents 1 to 4 disclose a condensation reaction product of an organopolysiloxane of a linear structure mainly having an MQ type organopolysiloxane resin and a D unit; and an MDQ type organopolysiloxane. While these cosmetic compositions can be expected to improve the film forming properties and feel derived from an organopolysiloxane condensation reaction product, compatibility with other oleophilic cosmetic raw materials may become insufficient, potentially causing deterioration in feel such as precipitation of the condensation reaction product, particularly when an organopolysiloxane condensation reaction product is blended in large quantities. Therefore, known organopolysiloxane condensation reaction products have a low degree of freedom in formulation design, and it has been difficult to fully utilize the advantages such as film forming properties based on the provision of both resin and linear structures. In addition, known organopolysiloxane condensation reaction products, particularly when blended in cosmetics, have room for further improved feel, such as the stickiness of a film derived from a resin structure.

In contrast, Patent Documents 5 and 6 disclose resin-linear organopolysiloxane block copolymers containing T units, acetoxylating and reacting with the terminals of polydimethylsiloxanes during synthesis. Unfortunately, since these copolymers are copolymers composed of a resin structure block primarily consisting of T units and a linear structure organopolysiloxane, sufficient performance as a film forming agent cannot be achieved, with room for improvement in the molecular structure thereof.

PRIOR ART DOCUMENTS

Patent Documents

[Patent Document 1] US 2007/0196309 A
[Patent Document 2] WO 2014/151464
[Patent Document 3] U.S. Pat. No. 7,261,877
[Patent Document 4] JP 08-143426 A
[Patent Document 5] WO 2014/040367
[Patent Document 6] WO 2014/152522

SUMMARY OF THE INVENTION

Problems to be Solved by the Invention

It is an object of the present invention to provide a novel resin-linear organopolysiloxane block copolymer, along with the use and production method thereof, which has a high degree of freedom in formulation due to excellent compatibility with other lipophilic starting materials, in addition to exhibiting excellent film forming properties and followability of a film, while the stickiness of a film or the like is suppressed.

Means for Solving the Problems

The resin-linear organopolysiloxane block copolymer according to the present invention includes: a resin structure (A1) block that has siloxane units represented by $R^1SiO_{3/2}$ (wherein $R^1$ represents a monovalent organic group, a hydroxyl group, or an alkoxy group having 1 to 6 carbon atoms) and $SiO_{4/2}$; and a linear structure (A2) block represented by $(R_2SiO_{2/2})_n$ (wherein n represents a number of 5 or more while R represents an alkyl group, a fluoroalkyl group, or an aryl group) in each molecule, wherein the resin structure (A1) and the linear structure (A2) are linked to each other by an Si—O—Si bond, and an Si atom bonded to the resin structure (A1) constitutes an $RSiO_{3/2}$ unit.

Further, the resin-linear organopolysiloxane block copolymer (A) preferably has a hydroxyl group (OH) content in the molecule of 1.50 mass % or more, more preferably 1.75 mass % or more, and even more preferably 2.00 mass % or more.

Further, the resin-linear organopolysiloxane block copolymer (A) is an $SiO_{4/2}$ unit in which 15 mol % or more, preferably 20 mol % or more, and more preferably 25 mol % or more of all $SiO_{4/2}$ units have hydroxyl groups on Si atoms.

The resin-linear organopolysiloxane block copolymer is preferably soluble in cinnamic acid methyl ester.

The resin-linear organopolysiloxane block copolymer may further have one or more functional groups selected from an alkyl group having 6 or more carbon atoms, a fluoroalkyl group, an Si-macromonomer, and an Si-dendrimer modifying group in the molecule.

In the resin-linear organopolysiloxane block copolymer, the linear structure (A2) block preferably has a silicon atom-bonded acyloxy group, an oxime group, or an alkoxy group in the molecule and is derived from an organopolysiloxane having a polysiloxane structure represented by $(R_2SiO_{2/2})_n$ (wherein n represents a number of 5 or more while R represents an alkyl group, a fluoroalkyl group, or an aryl group). Note that a silicon atom-bonded acyloxy group, an oxime group, or an alkoxy group is preferably introduced as an organodiacyloxysilyl group, a dioximesilyl group, or a dialkoxysilyl group at a terminal and particularly preferably constitutes an $RSiO_{3/2}$ unit bonded to the resin structure (A1) block during the formation reaction of the copolymer.

The composition according to the present invention preferably contains the resin-linear organopolysiloxane block copolymer and a solvent thereof. Particularly when the copolymer of the present invention is used in the application of a film forming agent, the solvent is preferably a volatile solvent.

The resin-linear organopolysiloxane block copolymer according to the present invention or the composition including the same can be suitably used in the following applications.

Film forming agent
Adhesion imparting agent
Sealant
Composition for an electronic material
Cosmetic composition or preparation for external use The resin-linear organopolysiloxane block copolymer according to the present invention can be suitably obtained by a production method having the following Steps (1) and (2).

Step (1): subjecting an organopolysiloxane having a hydroxyl group in the molecule and having a polysiloxane structure represented by $(R_2SiO_{2/2})_n$ (wherein n represents a number of 5 or more, while R represents an alkyl group, a fluoroalkyl group, or an aryl group) to diacyloxy silanization, dioxime silanization, or dialkoxy silanization, using one or more organotriacyloxysilanes, organotrioximesilanes, or organotrialkoxysilanes; and Step (2): subjecting an organopolysiloxane having a diacyloxysilyl group, a dioximesilyl group, or a dialkoxysilyl group in the molecule obtained by the Step (1); and a resin organopolysiloxane having a hydroxyl group in the molecule and having a siloxane unit represented by $SiO_{4/2}$ to a decarboxylation reaction, a deoximation reaction, or a dealcoholization reaction.

Effects of the Invention

The present invention can provide a novel resin-linear organopolysiloxane block copolymer, along with the use and production method thereof, and can particularly provide a copolymer having a structure or functional group content suitable for various applications including a film forming agent, along with a method for producing the same.

MODE FOR CARRYING OUT THE INVENTION

[Resin-Linear Organopolysiloxane Block Copolymer (A)]

The resin-linear organopolysiloxane block copolymer of the present invention has a structure in which a resin structure (A1) block that has siloxane units represented by $R^1SiO_{3/2}$ (wherein $R^1$ represents a monovalent organic group, a hydroxyl group or an alkoxy group having 1-6 carbon atoms) and $SiO_{4/2}$; and a linear structure (A2) block represented by $(R_2SiO_{2/2})_n$ (wherein n represents a number of 5 or more while R represents an alkyl group, a fluoroalkyl group or an aryl group) are connected by an Si—O—Si bond in each molecule, wherein in an Si—O—Si bond which links the resin structure (A1) block and the linear structure (A2) block to each other, an Si atom bonded to the resin structure (A1) constitutes an $R^1SiO_{3/2}$ unit. Hereinafter, the resin-linear organopolysiloxane block copolymer (A) may be simply referred to as "copolymer (A)" when the component is described.

The copolymer (A) has a resin structure (A1) block and a linear structure (A2) block. The resin structure (A1) block is a resinous (resin) organopolysiloxane structure, contains T units or Q units represented by $R^1SiO_{3/2}$ ($R^1$ is a monovalent organic group, a hydroxyl group, or an alkoxy group having 1 to 6 carbon atoms) and by $SiO_{4/2}$ as essential siloxane units, and forms partial structures consisting of resinous organopolysiloxanes in which a large number of Q units are primarily bonded. Such a resin structure is a partial structure which imparts film forming properties when the copolymer (A) of the present invention is incorporated into a cosmetic composition or a preparation for external use.

Examples of such resin structures (A1) include an MQ resin, an MDQ resin, an MTQ resin, an MDTQ resin, a TQ resin, and a TDQ resin, which consist of any combination including a triorganosiloxy unit (M unit) represented by $R^1_3SiO_{1/2}$ ($R^1$ is a monovalent organic group, a hydroxyl group, or an alkoxy group having 1 to 6 carbon atoms); and a diorganosiloxy unit (D unit) represented by $R^1_2SiO_{2/2}$ ($R^1$ is a monovalent organic group, a hydroxyl group, or an alkoxy group having 1 to 6 carbon atoms), in addition to the abovementioned T unit and Q unit. In particular, the MQ resin is preferable, and in the Si—O—Si bond connecting the resin structure (A1) block and the linear structure (A2) block, the T units may be preferably included only in the portion in which the Si atom bonded to the resin structure (A1) constitutes an $R^1SiO_{3/2}$ unit. Note that in relation to the linear structure (A2) described later, the resin structure (A1) does not include a partial structure in which 5 or more D units are consecutively included.

The functional groups $R^1$ on the siloxane unit constituting the resin structures (A1) are each independently a monovalent organic group, a hydroxyl group, or an alkoxy group having 1 to 6 carbon atoms. In particular, the functional groups $R^1$ include an alkyl group having 1 to 20 carbon atoms, a halogen-substituted alkyl group having 1 to 20 carbon atoms, an aryl group having 6 to 20 carbon atoms, a halogen-substituted aryl group having 6 to 20 carbon atoms, an aralkyl group having 7 to 20 carbon atoms, an alkenyl group having 2 to 20 carbon atoms, an acryl-containing group, a methacryl-containing group, an alkoxy group having 1 to 6 carbon atoms, and a hydroxyl group.

Specifically, the functional groups $R^1$ include alkyl groups such as a methyl group, an ethyl group, a propyl group, a butyl group, a pentyl group, a hexyl group, a heptyl group, an octyl group, a nonyl group, a decyl group, an undecyl group, and a dodecyl group; aryl groups such as a phenyl group, a tolyl group, a xylyl group, a naphthyl group, an anthracenyl group, a phenanthryl group, and a pyrenyl group; aralkyl groups such as a phenethyl group and a phenylpropyl group; groups in which some or all of the hydrogen atoms bonded to these groups are replaced with a halogen atom such as a fluorine atom, a chlorine atom, a bromine atom, or the like; alkoxy groups such as a methoxy group, an ethoxy group, or a propoxy group; alkenyl groups having 2 to 20 carbon atoms such as a vinyl group, an allyl group, a butenyl group, a pentenyl group, a hexenyl group, a heptenyl group, an octenyl group, a nonenyl group, a decenyl group, an undecenyl group, and a dodecenyl group; acrylic-containing groups such as a 3-acryloxypropyl group and a 4-acryloxybutyl group; methacryl-containing groups such as a 3-methacryloxypropyl group and a 4-methacryloxybutyl group; and hydroxyl groups.

From an industrial point of view, the functional group $R^1$ on the siloxane unit constituting the resin structure (A1) is preferably an alkyl group, a fluorine-substituted alkyl group, an aryl group, an alkenyl group, an alkoxy group, or a hydroxyl group and is preferably a group selected from a methyl group, an ethyl group, a propyl group, a phenyl group, a vinyl group, a hexenyl group, a methoxy group, an ethoxy group, and a hydroxyl group. In particular, when a large number of aryl groups such as phenyl groups are contained in the molecule, the refractive index of the polymer (A) is improved, while a highly transparent appearance is provided at the time of film forming, which is particularly preferable.

The organopolysiloxane resin raw material providing the resin structure (A1) block of the copolymer (A) preferably has a weight-average molecular weight in the range of from 500 to 20,000, more preferably in the range of from 1,000 to 15,000, and more preferably in the range of from 1,500 to 12,000. The organopolysiloxane resin raw material providing the resin structure (A1) block may be two or more kinds having different weight-average molecular weights, hydroxyl group contents, ratios of siloxane units (M, D, T, Q units), and the like. The weight-average molecular weight (weight-average molecular weight based on styrene polymer) of the resin structure (A1) block in the molecule of the copolymer (A) varies depending on the organopolysiloxane resin as a raw material and the degree of condensation reaction between the hydroxyl groups in the organopolysiloxane resin.

The linear structure (A2) is an unreactive block represented by $(R_2SiO_{2/2})_n$ (n is a number of 5 or more, R is an alkyl group, a fluoroalkyl group, or an aryl group) and has a structure in which diorganosiloxy units represented by $R_2SiO_{2/2}$ are connected in a chain form by at least 5 units or more. Such a linear structural (A2) block is a partial structure that gives flexibility and followability to the film formed by the copolymer (A). In the formula, n is the degree of polymerization of the diorganosiloxy unit constituting the partial structure, preferably in the range of from 5 to 1000 and more preferably in the range of from 5 to 500, 10 to 300, and 15 to 200. When n in the partial structure exceeds the above upper limit, the properties as a linear molecule derived from the linear structure are strongly expressed and the film forming properties or the like may be deteriorated in some cases. On the other hand, when n is less than the abovementioned lower limit, the properties as a linear molecule are not sufficient, preventing the characteristic physical properties of the copolymer (A) from being realized in some cases.

The functional group R on the diorganosiloxy unit constituting the linear structure (A2) is an alkyl group, a fluoroalkyl group, or an aryl group, which is unreactive with respect to the resin structure (A1) and the functional group in the same molecule, making it necessary to maintain the linear structure (A2) without causing a polymerization reaction such as a condensation reaction within the molecule. The alkyl group and the aryl group are the same groups as described above, with a methyl group or a phenyl group preferable from an industrial point of view.

The diorganopolysiloxane providing the linear structure (A2) block of the copolymer (A) is a chain organopolysiloxane in which the degree of polymerization of the diorganosiloxy unit having a hydroxyl group or a hydrolyzable functional group at the molecular chain end is within the above range (such as within the range of from 5 to 1000) and is preferably a diorganopolysiloxane in which the degree of polymerization of the diorganosiloxy unit is from 15 to 200 and has, at the molecular chain end, the hydroxyl group (silanol group); or a siloxysilyl end, a dioximesilyl end, or a dialkoxy silyl end derived from the silanol group described later.

[Resin/linear structure connecting portion of the copolymer (A)]

The copolymer (A) is characterized by having a structure in which the resin structure (A1) and the linear structure (A2) are connected by an Si—O—Si bond while an Si atom bonded to the resin structure (A1) constitutes an $RSiO_{3/2}$ unit. A plurality of partial structures connected by these Si—O—Si bonds may be included in the molecules, and all resin structure (A1) blocks preferably have $R^1SiO_{3/2}$ units at the bonding sites thereof. The functional group $R^1$ is the same group as above and preferably a group selected from a methyl group, an ethyl group, a propyl group, a phenyl group, a vinyl group, a hexenyl group, a methoxy group, an ethoxy group, and a hydroxyl group. The Si—O—Si bonds connecting the structures are siloxane bonds between silicon atoms constituting the resin structure (A1) or the linear structure (A2), the silicon atoms on the T unit or the Q unit represented by $R^1SiO_{3/2}$ or $SiO_{4/2}$ constituting the resin structure (A1) respectively, and the silicon atoms of the linear structure (A2) represented by $(R_2SiO_{2/2})_n$ (n is a number of 5 or more, and R is an alkyl group, a fluoroalkyl group, or an aryl group) form a partial structure (T-Dn) or (Q-Dn) as follows. In the copolymer (A), the Si atom bonded to the resin structure (A1) is required to constitute an $RSiO_{3/2}$ unit and always has the following partial structure (T-Dn) in the molecule.

Partial structure (T-Dn)

[Formula 1]

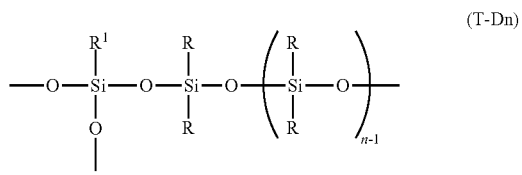

(T-Dn)

Partial structure (Q-Dn)

[Formula 2]

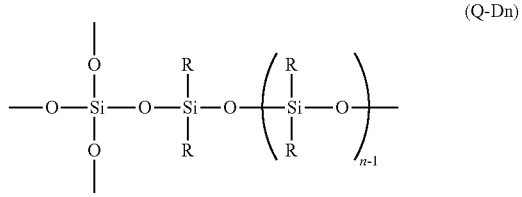

(Q-Dn)

In the above partial structure, the end of the left Si—O-bond constituting the T unit or the Q unit is bonded to a hydrogen atom or another siloxane unit constituting the resin structure (A1), respectively. However, at least one of Si—O-bonds is bonded to another siloxane unit constituting the resin structure (A1). On the other hand, the end of the right Si—O-bond is bonded to another siloxane unit, triorganosiloxy unit (M unit), or hydrogen atom that forms a linear structure (A2) or a resin structure (A1). Needless to say, a silanol group (Si—OH) is formed when a hydrogen atom is bonded to the end of the Si—O-bond.

While there must be at least one of the above partial structures in the molecule, it may have two or more of the above partial structures. A resin-linear organopolysiloxane block copolymer having at least one of the partial structures (T-Dn) in the molecule thereof is required from the viewpoint of compatibility and affinity with lipophilic raw materials.

Such partial structures (T-Dn) may suitably be constituted by condensation reacting an organopolysiloxane having a linear structure with a diacyloxysilyl end, a dioxime silyl end, or a dialkoxysilyl end with an organopolysiloxane having a resin structure. More specifically, a resin-linear organopolysiloxane block copolymer can be obtained by the production method thereof having:

Step (I): condensation reacting an organopolysiloxane having a silanol end (—OH) with an organotriacyloxysilane, an organotrioximesisilane, or an organotrialkoxysilane to form a linear structure organopolysiloxane having a siloxysilyl end, a dioximesilyl end, or a dialkoxy silyl; and Step (II): after Step (I), subjecting a linear structure organopolysiloxane having a diacyloxysilyl end, a dioximesilyl end, or a dialkoxysilyl end; and a resin structure organopolysiloxane having a hydroxyl group in the molecule and having a siloxane unit represented by $SiO_{4/2}$ to a decarboxylation reaction, a deoximation reaction, or a dealcoholization reaction to obtain a resin-linear organopolysiloxane block copolymer having an Si—O—Si bond, wherein an Si atom bonded to the resin structure constitutes an $RSiO_{3/2}$ unit.

Here, the organopolysiloxane having a resin structure having a siloxane unit represented by $SiO_{4/2}$ used in Step (II) is particularly preferably an MQ resin.

In Step (I) above, since the $RSiO_{3/2}$ units of the connecting moiety are derived from triacyloxysilane, trioxymylane, or trialkoxysilane, the functional groups on the $RSiO_{3/2}$ units bonded to the resin structures (A1) in the polymer can be designed by selecting triacyloxysilane, trioxymylane, or trialkoxysilane having particular functional groups. Specifically, the functional group R bonded to silicon atoms constituting an organotriacetoxysilane represented by $R(CH_3COO)_3Si$ is introduced on the $RSiO_{3/2}$ units of the connecting portion. Therefore, by using phenyltriacetoxysilane represented by $(Ph)(CH_3COO)_3Si$ or alkyltriacetoxysilane represented by $R^2(CH_3COO)_3Si$ ($R^2$ is an alkyl group having 3 to 20 carbon atoms), a resin-linear organopolysiloxane block copolymer containing a $PhSiO_{3/2}$ (Ph is a phenyl group) unit or an $R^2Si_{3/2}$ ($R^2$ is an alkyl group having 3 to 20 carbon atoms) unit can be easily obtained.

The copolymer (A) may have an aryl group such as a phenyl group in the molecule, and in particular, a triorganosiloxy group constituting the end of a resin structure or a linear structure may have at least one or more aryl groups. The high content of aryl groups in the copolymer (A) of the present invention tends to increase the refractive index of the polymer as a whole, in addition to improving the optical transparency.

The copolymer (A) may further have one or more functional groups selected from an alkyl group having 6 or more carbon atoms, a fluoroalkyl group, an Si-macromonomer, and an Si-dendrimer modifying group in the molecule. Since these functional groups have high hydrophobicity or water repellency, along with affinity for specific components, the film formed by the copolymer (A) may be further improved in functionality in some cases.

The copolymer (A) may have a triorganosiloxy group having at least two aryl groups in the molecule and may contain $R^4R^5R^6SiO_{1/2}$ units ($R^4$ to $R^6$ are each independently a monovalent organic group, with at least two of these being aryl groups). Such triorganosiloxy groups may be triorganosiloxy groups having at least two phenyl groups or triorganosiloxy groups having three phenyl groups. Moreover, a triorganosiloxy group having aryl groups other than at least two phenyl groups may be used. Such a triorganosiloxy group is introduced by condensation reactions using an organosilane represented by $R^4R^5R^6SiX$ ($R^4$ to $R^6$ are each independently monovalent organic groups, at least two of which are aryl groups, and X is a hydroxyl group or a hydrolyzable group) as a raw material.

[Hydroxyl Group Content of Copolymer (A)]

From the viewpoint of compatibility and affinity with other cosmetic raw materials, the copolymer (A) preferably has a hydroxyl group in the molecule and preferably has a hydroxyl group (OH) content in the molecule of 1.50 mass % or more, more preferably 1.75 mass % or more, more preferably 2.0 mass % or more, and particularly preferably 2.25 mass % or more. Most preferably, the hydroxyl group (OH) content of the copolymer is in the range of from 2.25 to 3.50 mass %. While the copolymer may be a single type or a mixture of copolymers having two different hydroxyl group (OH) contents, the average value of the hydroxyl group (OH) contents of these copolymers is preferably in the above range.

In particular, the copolymer (A) can preferably be obtained by condensation reacting an organopolysiloxane having a linear structure with a diacyloxysilyl end, a dioxime silyl end, or a dialkoxysilyl end and an organopolysiloxane having a resin structure having a siloxane unit represented by $SiO_{4/2}$. Since the reaction at the siloxysilyl end, the dioximesilyl end, or the dialkoxysilyl end proceeds selectively with respect to the hydroxyl group on the organopolysiloxane having the resin structure, many hydroxyl groups react between the organopolysiloxanes having the resin structure and it is possible to synthesize a resin-linear organopolysiloxane block copolymer in which a competitive reaction which lowers the hydroxyl group (OH) content of the copolymer hardly occurs and a large number of hydroxyl groups (OH) on the resin structure are maintained. Therefore, the copolymer (A) of the present invention can be designed to have a regular structure and a high hydroxyl group (OH) content on the resin structure as compared with the conventional resin/linear organopolysiloxane condensation product. For example, in the case of a reaction product of a polysiloxane resin of the MQ type having a known hydroxyl group and a chain polysiloxane having a hydrolyzable terminal such as a hydroxyl group, the condensation reaction between the resins and the condensation reaction of the chain polysiloxane proceed competitively, the hydroxyl group is consumed in the reaction between the resins, and a random intermolecular bond tends to be formed, such that the affinity with other lipophilic raw materials and the film forming ability may be lowered as compared with the copolymer (A) of the present invention.

More specifically, the copolymer (A) has $SiO_{4/2}$ units and 15 mol % or more of all $SiO_{4/2}$ units preferably have hydroxyl groups on Si atoms. The $SiO_{4/2}$ unit (Q) unit is a siloxane unit mainly constituting a resin structure and the high proportion of Q units having a hydroxyl group on the Si atom means that a large number of hydrophilic functional groups are included in the resin portion of the polymer (A) and the affinity with other cosmetic raw materials is improved along with the film forming properties. In this respect, preferably 20 mol % or more, more preferably 25 mol % or more, and most preferably 27.5 to 40.0 mol % of all $SiO_{4/2}$ units of the copolymer (A) have hydroxyl groups on Si atoms. Even when a polysiloxane resin having a large number of hydroxyl groups is used as a raw material, the amount of hydroxyl groups decreases and the molecular structure of the copolymer randomizes when a large number of condensation reactions between resin raw materials proceed when forming the copolymer (A), such that the copolymer (A) has the partial structure (T-Dn) described above, and it is particularly preferable that the copolymer (A) has a regular resin-linear structure.

[weight-average molecular weight of the total copolymer (A)]

The copolymer (A) is preferably composed of a resin structure (A1) block and a linear structure (A2) block bonded by the abovementioned connecting structure, wherein the molecular weight distribution thereof can be controlled to some extent by the organopolysiloxane resin as a raw material, the chain diorganopolysiloxane, and the degree of condensation reaction; however, from the viewpoint of the function as a film forming agent and compatibility with other raw materials, the weight-average molecular weight specified from the molecular weight distribution using styrene polymer as a standard is preferably within the range of from 5,000 to 100,000, particularly preferably within the range of from 10,000 to 50,000, and within the range of from 12,000 to 40,000. The cosmetic composition or preparation for external use of the present invention may be combined with the two or more copolymers (A) having different structures or molecular weight distributions.

[Mass Ratio of Resin/Linear Structure Block of Copolymer (A)]

The copolymer (A) is composed of a resin structure (A1) block and a linear structure (A2) block bonded by the abovementioned connecting structure, wherein the mass ratio of both blocks in the molecule can be controlled by the amount of the organopolysiloxane resin and the chain diorganopolysiloxane used as raw materials. Suitably, the organopolysiloxane resin constituting the resin structure (A1) block and the chain diorganopolysiloxane constituting the linear structure (A2) block can be reacted at a mass ratio of from 10:90 to 95:5, and from the viewpoint of film forming properties of the obtained copolymer (A), an excess of the resin, that is, a mass ratio of from 50:50 to 95:5 is preferable, with a mass ratio of from 60:40 to 90:10 particularly preferable. When the mass ratio of the resin structure (A1) block in the molecule is within the abovementioned range as derived from the raw material, the film forming properties with little stickiness which are hard and excellent in sensation during use is realized while maintaining followability and flexibility of the film derived from the linear structure (A2) block. Incidentally, in the case of a resin-linear organopolysiloxane block copolymer having no $R^1SiO_{3/2}$ units in molecules thereof, even within the abovementioned mass ratio, the film forming properties are insufficient and stickiness of the film, lowering of the affinity with other cosmetic raw material components, and the like may occur.

[Compatibility of the Copolymer (A)]

The copolymer (A) is excellent in compatibility with other lipophilic raw materials and when used in combination with a solvent (B) described later, it has a feature of being compatible with lipophilic raw materials of ½ or more the mass of the copolymer (A), and the film forming performance thereof does not deteriorate. For example, for cinnamic acid methyl ester, in particular, octyl methoxycinnamate (p-methoxycinnamate ethylhexyl cinnamate) as a representative and general purpose lipophilic raw material, the copolymer (A) exhibits solubility in the presence of the solvent (B) described below. For a 20 mass % solution of the solvent (B), the copolymer (A) uniformly dissolves with cinnamic acid methyl ester having the same, preferably 1.2-fold, and more preferably 1.5-fold or more mass as that of the copolymer (A) in the solution, and the separation and precipitation of cinnamic acid methyl ester preferably do not occur over time. With such properties, the copolymer (A) is advantageously usable in a wide range of dosage forms and formulations as a film forming agent because of the high degree of freedom of formulation design as a lipophilic raw material and the excellent compounding stability compared with copolymers having a known resin-linear structure within the same molecule in the related art.

[Solvent (B)]

The cosmetic composition or preparation for external use is characterized by containing the copolymer (A) described above, and since the copolymer (A) is in a solid to viscous semi-solid state at room temperature, it is preferable to blend the copolymer (A) in a form dissolved in the solvent (B) from the viewpoint of handling workability. Since the copolymer (A) is excellent in affinity with other cosmetic raw materials and has high solubility, the solvent (B) can utilize a physiologically acceptable oil agent without any particular limitation, and in particular, the solvent (B) is preferably at least one kind in a liquid state at from 5 to 100° C. selected from the group consisting of silicone oil, non-polar organic compound, and low polarity organic compound and may be a combination of two or more kinds. Moreover, from the viewpoint of the sensation during the use of the cosmetic composition or the preparation for external use of the present invention and the workability when the copolymer (A) is handled as a film forming agent, the solvent (B) is preferably a volatile solvent (B1), and a solvent containing a volatile silicone oil is particularly preferable.

Silicone oils are hydrophobic and their molecular structure may be any of cyclic, linear, or branched. The viscosities of silicone oils at 25° C. are usually within the range of from 0.65 to 100,000 mm²/s and preferably within the range of from 0.65 to 10,000 mm²/s.

Silicone oils include, for example, linear organopolysiloxanes, cyclic organopolysiloxanes, and branched organopolysiloxanes. Among these, volatile linear organopolysiloxanes, cyclic organopolysiloxanes, and branched organopolysiloxanes are preferable, with octamethylcyclotetrasiloxane (D4), decamethylcyclopentasiloxane (D5), or chain dimethylpolysiloxane having viscosities ranging from 0.65 to 10 mm²/s at 25° C. particularly preferable as initial dispersing solvents of the present polymer (A).

The solvent (B) may be added to the composition of the present invention as the initial dispersion solvent of the copolymer (A) or may be added to other components or as independent components, with the type/combination thereof not particularly limited.

From the viewpoint of handling workability as a film forming agent, while it is suitable to include a volatile solvent (B1) as an initial dispersion solvent of the copolymer (A), a non-volatile solvent (B) may be added as another oil agent. The compounding amount is not particularly limited, but is preferably from 3 to 60 mass %, more preferably from 4 to 50 mass %, and still more preferably from 5 to 40 mass %, based on the total mass of the cosmetic composition or the preparation for external use.

In addition to silicone oils, non-polar organic compounds and low-polarity organic compounds (for example, hydrocarbon oils and fatty acid ester oil oils and fats), higher alcohols, higher fatty acids, fluorine-based oils, etc. may be used as solvents, or two or more of these may be used in combination.

[Film Forming Agent]

The resin-linear organopolysiloxane block copolymer according to the present invention forms a uniform and hard film having little stickiness on a substrate by removing a solvent. Further, since the film has flexibility and followability to substrates derived from a linear structure, problems such as cracking and peeling are less likely to occur compared with known resin based film forming agents, leading to excellent durability. Moreover, due to the excellent affinity and compatibility thereof with lipophilic industrial raw materials such as dyes or ultraviolet light protecting components, functional films on which these components are supported in films can be formed.

In addition, when used in cosmetics or preparations for external use, various tissues such as hair, skin, and the body can be protected by film formation on the human body while various active components can be supported on various tissues. In particular, since the copolymer has flexibility and followability derived from a linear structure, the copolymer has flexibility while being a hard and strong film derived from a resin, along with high compatibility and affinity with various lipophilic raw materials. Therefore, it may be used in a form in which a package or capsule is formed by coating an active ingredient.

[Adhesion Imparting Agent]

The resin-linear organopolysiloxane block copolymer according to the present invention has excellent adhesion to substrates and therefore functions as an adhesion imparting agent when used in combination with other curable compositions or film forming components. For example, when blended in a paint, coating agent, etc., due to the excellent compatibility thereof with other cured film forming components, the film properties and flexibility derived from the copolymer (A) are imparted to a cured film such as paint, improving adhesion with the substrate.

[Sealant]

The resin-linear organopolysiloxane block copolymer according to the present invention is active to condensation reactions because it has a large number of hydroxyl groups in the resin structure block in the molecule. Therefore, the addition thereof to a known condensation reaction curing system enables its use as a sealant with excellent transparency. In particular, by containing a main agent or an additive in a curable composition having a condensation reaction catalyst, it is possible to form a flexible and strong cured product having excellent affinity with other curable components.

[Composition for Electronic Materials]

The resin-linear organopolysiloxane block copolymer according to the present invention can be used as a film forming agent, an adhesion imparting agent, and a sealant for forming a cured product; and as a composition for use in electronic materials such as semiconductor circuits, optical semiconductors, and solar cells. For example, a semiconductor circuit or an optical semiconductor element can be sealed or cure coated by a cured product containing the resin-linear organopolysiloxane block copolymer according to the present invention.

[Cosmetic Composition or Preparation for External Use]

The resin-linear organopolysiloxane block copolymer according to the present invention is particularly useful in a film forming agent as a cosmetic raw material and can be blended into various cosmetic compositions or preparations for external use. In particular, since the copolymer has excellent compatibility with other cosmetic raw materials, the composition or the preparation has a high degree of freedom of formulation design. It is possible to provide a cosmetic composition or a preparation for external use containing a resin-linear organopolysiloxane block copolymer that has excellent film forming properties and film followability, with the stickiness of the film being suppressed, etc.

EXAMPLES

The cosmetic composition or the preparation for external use and the cosmetic raw material composition of the present invention will be explained in detail with reference to examples and comparative examples. In the formula, Me represents a methyl group and Et represents an ethyl group. In addition, unless otherwise specified, in the examples, the M unit is a siloxane unit represented by the $Me_3SiO_{1/2}$, the Q unit is a siloxane unit represented by the $SiO_{4/2}$, and the MQ resin means a resinous organopolysiloxane (resin) having a hydroxyl group bonded on the M unit, the Q unit, and silicon atoms of the Q unit. The average degree of polymerisation of the dimethylsiloxane units of polydimethylsiloxane was calculated from the ratio of the intensities of the peaks to the Si atoms constituting both ends using $^{29}$Si-NMR. The weight-average molecular weight was determined as a value converted to standard polystyrene by GPC.

Example 1: Copolymer a1

An equimolar mixture of 0.8 grams (3.53 mmol) of methyltriacetoxysilane and ethyltriacetoxysilane was added to a solution of 6 grams (1.68 mmol) of polydimethylsiloxane capped with silanol ($—SiMe_2(OH)$) groups at both ends (an average degree of polymerization of 48); and 10 grams of n-heptane and then stirred at room temperature for 30 minutes. Upon $^{29}$SiNMR analysis, it was found that the SiOH group completely disappeared and diacetoxysilylated. The solution was then added to a mixed solution of 34 grams of trimethyl siloxysilicate having a molar ratio of M units ($Me_3SiO_{1/2}$) to Q units ($SiO_{4/2}$) of 54:46, an OH group content derived from silanol groups of 3.13 wt %, a ratio of Q units bound to OH groups to total Q units of 26.5%, and a weight-average molecular weight of 2970; and 50 grams of n-heptane and then heated and stirred for 2 hours while removing a by-product aqueous acetic acid aqueous solution by azeotropic dehydration. Water was added and heated to stir for 1 hour and allowed to stand to remove the lower layer. This operation was further repeated to completely remove the acetic acid. After azeotropic dehydration, the low boiling point substances were removed by heating to give the MQ resin-polydimethylsiloxane copolymer (copolymer a1).

The copolymer a1 is designed to have a mass ratio of MQ resin as a raw material to chain polydimethylsiloxane of 85:15 and contains T units represented by $MeSiO_{3/2}$ and $EtSiO_{3/2}$ which are bonded to Si atoms constituting a resin structure at a connecting site (Si—O—Si) of a resin structure and a linear structure by way of diacetoxysilylation in a condensation reaction.

Partial Structure of the Copolymer a1:

MQ resin block (Si)-T unit (Si)—O—(Si) polydimethylsiloxane block

The residual OH group content in the copolymer a1 was 2.28 mass %, the ratio of Q units bound to OH groups to total Q units was 20.5 mol %, and the weight-average molecular weight thereof was 18500.

Example 2: Copolymer a2

An equimolar mixture of 1.07 grams (4.71 mmol) of methyltriacetoxysilane and ethyltriacetoxysilane was added to a solution of 8 grams (2.24 mmol) of polydimethylsiloxane capped with silanol ($—SiMe_2(OH)$) groups at both ends (an average degree of polymerization of 48); and 10 grams of n-heptane and then stirred at room temperature for 30 minutes. Upon $^{29}$SiNMR analysis, it was found that the SiOH group completely disappeared and diacetoxysilylated. The solution was then added to a mixed solution of 25.6 grams of trimethyl siloxysilicate having a molar ratio of M units (Me$_3$SiO$_{1/2}$) to Q units (SiO$_{4/2}$) of 54:46, an OH group content derived from silanol groups of 3.13 wt %, a ratio of Q units bound to OH groups to total Q units of 26.5%, and a weight-average molecular weight of 2970; 6.4 grams of trimethyl siloxysilicate having a molar ratio of M units (Me$_3$SiO$_{1/2}$) to Q units (SiO$_{4/2}$) of 51:49, an OH group content derived from silanol groups of 2.74 wt %, a ratio of Q units bound to OH groups to total Q units of 23.9%, and a weight-average molecular weight of 7400; and 50 grams of n-heptane and then heated and stirred for 2 hours while removing a by-product aqueous acetic acid aqueous solution by azeotropic dehydration. 5 grams of water was added and heated to stir for 1 hour and allowed to stand to remove the lower layer. This operation was repeated to completely remove the acetic acid. After azeotropic dehydration, the low boiling point substances were removed by heating to give the MQ resin-polydimethylsiloxane copolymer (copolymer a2).

The copolymer a2 is designed to have a mass ratio of MQ resin as a raw material to chain polydimethylsiloxane of 80:20 and contains T units represented by MeSiO$_{3/2}$ or EtSiO$_{3/2}$ which are bonded to Si atoms constituting a resin structure at a connecting site (Si—O—Si) of a resin structure and a linear structure by way of diacetoxysilylation in a condensation reaction. Since methyltriacetoxysilane and ethyltriacetoxysilane used for diacetoxysilylation are equimolar, the ratio of the abovementioned T units is 1:1.

Partial Structure of the Copolymer a2:
MQ resin block (Si)-T unit (Si)—O—(Si) polydimethylsiloxane block The residual OH group content in copolymer a2 was 2.07 mass %, the ratio of Q units bound to OH groups to total Q units was 19.3 mol %, and the weight-average molecular weight thereof was 28800.

Comparative Example: Copolymer c without T Unit 1 gram of 28 wt % ammonia water was then added to a mixed solution of 6 grams (1.68 mmol) of silanol (—SiMe$_2$(OH)) polydimethylsiloxane at both ends (an average degree of polymerization of 48); 34 grams of trimethyl siloxysilicate having a molar ratio of M units (Me$_3$SiO$_{1/2}$) to Q units (SiO4/2) of 54:46, an OH group content derived from silanol groups of 3.13 wt %, a ratio of Q units bound to OH groups to total Q units of 26.5%, and a weight-average molecular weight of 2970; and 60 grams of n-heptane and then heated and stirred at 40° C. for 6 hours. Subsequently, the by-product water was heated and stirred for 1 hour while removing a by-product water by azeotropic dehydration. The low boiling point substances were removed by heating to give the MQ resin-polydimethylsiloxane condensation product (copolymer c).

The copolymer c does not contain a component constituting a T unit and has a partial structure in which a resin structure and a linear structure are simply bonded via a siloxane bond. The residual OH group content in copolymer c was 1.42 mass %, the ratio of Q units bound to OH groups to total Q units was 13.2 mol %, and the weight-average molecular weight thereof was 23200.

Example 1, 2 and Comparative Example 1, 2

The compositions according to the examples using the copolymer a1 and the copolymer a2 described above and the comparative examples using the copolymer c described above and conventional MQ silicone resins (MQ1600 manufactured by Dow Corning Corporation) were prepared and evaluated in the following manner.

Solubility evaluation: Polymers (the respective copolymers or MQ-silicone resins) and dimethylpolysiloxane (viscosity: 2 mPas·s, volatile) were dissolved beforehand in the parts by mass shown in Table 1, and then other components were added and stirred to confirm the appearance thereof.

Film followability: A 20% dimethylpolysiloxane (viscosity: 2 mPas·s, volatile) solution of the respective polymers was applied to a commercially available latex film, and then the solution was dried to form a film of about 50 µm on the latex film. Latex membranes were subsequently repeatedly stretched and the appearance of the films examined.

Stickiness: Solutions of 20% dimethylpolysiloxane (viscosities: 2 mPas·s, volatile) of the respective polymers were coated on a glass plate and dried to form a film, and then the stickiness was evaluated by contacting the glass plate.

Contact angle (water): 20% dimethylpolysiloxane (viscosities: 2 mPas·s, volatile) solutions of the respective polymers were coated on a glass plate and dried to form a film, and then the contact angle of water was measured by an automated contact angle meter (manufactured by Kyowa Interface Science Co., Ltd).

Contact angle (artificial sebum): 20% dimethylpolysiloxane (viscosities: 2 mPas·s, volatile) solutions of the respective polymers were coated on a glass plate and dried to form a film, and then the contact angle of artificial sebum was measured by an automated contact angle meter (manufactured by Kyowa Interface Science Co., Ltd).

In Examples 1, 2 and Comparative Example 1, copolymers prepared in Examples 1 and 2 and Comparative Example 1, respectively, were blended. In Comparative Example 2, an MQ1600 manufactured by Dow Corning Corporation was blended.

TABLE 1

| Experiment Example | Example 1 | Example 2 | Comparative Example 1 | Comparative Example 2 |
|---|---|---|---|---|
| Polymer | 3 | 3 | 3 | 3 |
| Uvinul A | | 2 | | |
| Octyl methoxycinnamate | | 5 | | |
| Octocrylene | | 3 | | |
| Isotridecyl isononanoate | | 9 | | |
| Dimethyl polysiloxane (viscosity: 2 mPa · s) | | 12 | | |
| Solubility | Dissolution | Dissolution | Separated | Dissolution |
| Film followability | Not changed | Not changed | Not changed | Cracks |
| Stickiness | No cracks | No cracks | Cracks generated | Cracks generated |
| Contact angle (water) | 102 | 100 | 101 | 96 |
| Contact angle (artificial sebum) | 57 | 49 | 61 | 31 |

As described in the above examples, the copolymers a1 and a2 having T units at the bonding sites were uniformly dissolved with other cosmetic raw material components, were excellent in sensation during use, and were able to realize film forming properties having high skin followability. On the other hand, in the copolymer c obtained in the comparative example, the other cosmetic raw material components were separated and not only was the compounding stability inferior, but also only a solid adhesive film was obtained. Moreover, in the evaluations using MQ1600, since it was a hard film derived from a resin, there was no skin followability, resulting in cracks. In addition, the contact angle evaluation of the Examples was comparable and equivalent to that of the Comparative Examples in both water and artificial sebum. From the above, it is possible to confirm the usefulness of a film forming agent (and various compositions containing it) excellent in compounding stability, sensation during use, and skin followability using the copolymers a1 and a2 of the present invention, unlike the known film forming agents.

The invention claimed is:

1. A resin-linear organopolysiloxane block copolymer comprising:
    a resin structure (A1) block that has siloxane units represented by $R^1SiO_{3/2}$ and $SiO_{4/2}$ wherein $R^1$ represents a monovalent organic group, a hydroxyl group, or an alkoxy group having 1 to 6 carbon atoms; and
    a linear structure (A2) block represented by $(R_2SiO_{2/2})_n$ wherein n represents a number of 5 or more while R represents an alkyl group, a fluoroalkyl group, or an aryl group in each molecule;
    wherein the resin structure (A1) and the linear structure (A2) are linked to each other by an Si—O—Si bond, wherein one of the Si atoms of the Si—O—Si bond is present in an $RSiO_{3/2}$ unit; and
    wherein 15 mol % or more of all $SiO_{4/2}$ units are $SiO_{4/2}$ units having hydroxyl groups on Si atoms.

2. The resin-linear organopolysiloxane block copolymer according to claim 1, wherein a hydroxyl group (OH) content within the molecule is 1.50 mass % or more.

3. The resin-linear organopolysiloxane block copolymer according to claim 2, wherein the hydroxyl group (OH) content within the molecule is 1.75 mass % or more.

4. The resin-linear organopolysiloxane block copolymer according to claim 1, which is soluble in cinnamic acid methyl ester.

5. The resin-linear organopolysiloxane block copolymer according to claim 1, further comprising: one or more functional groups selected from the group consisting of an alkyl group having 6 or more carbon atoms, a fluoroalkyl group, an Si-macromonomer, and an Si-dendrimer modifying group in the molecule.

6. A composition comprising:
    (A) the resin-linear organopolysiloxane block copolymer according to claim 1; and
    (B) a solvent.

7. The composition according to claim 6, wherein the solvent (B) is a volatile solvent (B1).

8. A film forming agent comprising: the resin-linear organopolysiloxane block copolymer according to claim 1.

9. An adhesion imparting agent comprising: the resin-linear organopolysiloxane block copolymer according to claim 1.

10. A sealant comprising: the resin-linear organopolysiloxane block copolymer according to claim 1.

11. A composition for an electronic material comprising: the resin-linear organopolysiloxane block copolymer according to claim 1.

12. A cosmetic composition or a preparation for external use comprising: the resin-linear organopolysiloxane block copolymer according to claim 1.

13. A method for producing the resin-linear organopolysiloxane block copolymer according to claim 1, the method comprising:
    Step (1): subjecting an organopolysiloxane having a hydroxyl group in the molecule and having a polysiloxane structure represented by $(R_2SiO_{2/2})_n$ wherein n represents a number of 5 or more while R represents an alkyl group, a fluoroalkyl group, or an aryl group
        to diacyloxy silanization, dioxime silanization, or dialkoxy silanization, using one or more organotriacyloxysilanes, organotrioximesilanes, or organotrialkoxysilanes; and
    Step (2): subjecting an organopolysiloxane having a diacyloxysilyl group, a dioximesilyl group, or a dialkoxysilyl group in the molecule obtained by the Step (1); and
    a resin organopolysiloxane having a hydroxyl group in the molecule and having a siloxane unit represented by $SiO_{4/2}$,
    to a decarboxylation reaction, a deoximation reaction, or a dealcoholization reaction.

* * * * *